(12) United States Patent
Schlottau et al.

(10) Patent No.: US 8,700,116 B2
(45) Date of Patent: Apr. 15, 2014

(54) SENSOR SYSTEM WITH PRESSURE APPLICATION

(75) Inventors: Friso Schlottau, Lyons, CO (US); Neville DeWitt Pierrat, Golden, CO (US); Sarah Hayman, Boulder, CO (US); Donald R. Sandmore, Lyons, CO (US)

(73) Assignee: Covidien LP, Mansfield, MA (US)

( * ) Notice: Subject to any disclaimer, the term of this patent is extended or adjusted under 35 U.S.C. 154(b) by 79 days.

(21) Appl. No.: 13/248,733

(22) Filed: Sep. 29, 2011

(65) Prior Publication Data

US 2013/0085356 A1  Apr. 4, 2013

(51) Int. Cl.
*A61B 5/1455* (2006.01)

(52) U.S. Cl.
USPC ............ 600/344; 600/310; 600/323; 600/340

(58) Field of Classification Search
USPC .................................................. 600/309–344
See application file for complete search history.

(56) References Cited

U.S. PATENT DOCUMENTS

| | | | |
|---|---|---|---|
| 4,685,464 A | 8/1987 | Goldberger et al. | |
| 4,825,872 A | 5/1989 | Tan et al. | |
| 4,825,879 A | 5/1989 | Tan et al. | |
| 5,209,230 A | 5/1993 | Swedlow et al. | |
| 5,217,012 A | 6/1993 | Young et al. | |
| 5,224,478 A | 7/1993 | Sakai et al. | |
| 5,237,994 A | 8/1993 | Goldberger | |
| 5,413,099 A | 5/1995 | Schmidt et al. | |
| 5,427,093 A | 6/1995 | Ogawa et al. | |
| 5,452,717 A | 9/1995 | Branigan et al. | |
| 5,709,205 A | 1/1998 | Bukta | |
| RE36,000 E | 12/1998 | Swedlow et al. | |
| 5,891,026 A | 4/1999 | Wang et al. | |
| 5,919,133 A | 7/1999 | Taylor et al. | |
| 5,999,834 A | 12/1999 | Wang et al. | |
| 6,385,821 B1 | 5/2002 | Modgil et al. | |
| 6,519,487 B1 | 2/2003 | Parker | |
| 6,606,512 B2 | 8/2003 | Muz et al. | |
| 6,731,963 B2 | 5/2004 | Finarov et al. | |
| 6,748,254 B2 | 6/2004 | O'Neil et al. | |
| 6,839,585 B2 * | 1/2005 | Lowery et al. | 600/344 |
| 7,047,056 B2 | 5/2006 | Hannula et al. | |
| 7,113,815 B2 | 9/2006 | O'Neil et al. | |
| 7,190,987 B2 | 3/2007 | Lindekugel et al. | |
| 7,225,006 B2 | 5/2007 | Al-Ali et al. | |
| 2003/0171662 A1 | 9/2003 | O'Connor et al. | |
| 2004/0147821 A1 | 7/2004 | Al-Ali et al. | |
| 2005/0043600 A1 | 2/2005 | Diab et al. | |
| 2005/0228248 A1 | 10/2005 | Dietiker | |

(Continued)

FOREIGN PATENT DOCUMENTS

EP        430340        6/1991
EP       1807001        7/2007

(Continued)

*Primary Examiner* — Eric Winakur
*Assistant Examiner* — Marjan Fardanesh
(74) *Attorney, Agent, or Firm* — Fletcher Yoder

(57) ABSTRACT

Embodiments of the present disclosure relate to sensors for applying pressure to a patient's tissue. According to certain embodiments, the sensors may include one or more deformable elements that hold the optical components of the sensor against the tissue with an appropriate amount of pressure. In additional embodiments, such sensors may include a rigid one-piece sensor body that incorporates a deformable element to facilitate fine-fitting of the sensor against the tissue.

15 Claims, 9 Drawing Sheets

(56) References Cited

U.S. PATENT DOCUMENTS

| | | |
|---|---|---|
| 2006/0079794 A1 | 4/2006 | Liu et al. |
| 2006/0195028 A1 | 8/2006 | Hannula et al. |
| 2006/0253010 A1 | 11/2006 | Brady et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0276700 A1 | 12/2006 | O'Neil et al. |
| 2007/0032716 A1 | 2/2007 | Raridan et al. |
| 2007/0106132 A1 | 5/2007 | Elhag et al. |
| 2007/0129622 A1 | 6/2007 | Bourget et al. |
| 2007/0260130 A1 | 11/2007 | Chin |
| 2008/0076980 A1 | 3/2008 | Hoarau |
| 2008/0076981 A1 | 3/2008 | Hoarau |
| 2008/0076994 A1 | 3/2008 | Hoarau |
| 2008/0076996 A1 | 3/2008 | Hoarau |
| 2008/0097560 A1 | 4/2008 | Radziunas et al. |
| 2010/0076337 A1* | 3/2010 | Medina .................. 600/549 |

FOREIGN PATENT DOCUMENTS

| | | |
|---|---|---|
| JP | 6269430 | 9/1994 |
| JP | 7236625 | 9/1995 |
| JP | 20237170 | 9/2000 |
| JP | 23275192 | 9/2003 |
| JP | 28119026 A2 | 5/2008 |
| WO | WO2006110488 A2 | 10/2006 |
| WO | WO2006110488 A3 | 10/2006 |
| WO | WO2006110488 C2 | 5/2007 |

* cited by examiner

SENSOR SYSTEM WITH PRESSURE APPLICATION

BACKGROUND

The present disclosure relates generally to medical devices and, more particularly, to sensors for determining physiological parameters.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine. For example, photoplethysmography is a common technique for monitoring physiological characteristics of a patient, and one device based upon photoplethysmography techniques is commonly referred to as a pulse oximeter. Pulse oximeters may be used to measure and monitor various blood flow characteristics of a patient. A pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters or other photoplethysmography-based devices typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry measurement often involves placement of a sensor on a patient's tissue, typically via an adhesive sensor, a clip-style sensor, or a sensor that may be fitted through pressure contact with the tissue. Because these sensors are typically worn for several hours before the sensor is repositioned, pulse oximetry sensors may slightly deform the underlying tissue if the pressure contact is too great. Deformed tissue may lead to reduced measurement accuracy in cases where pressure from the sensor alters the blood flow into the tissue, leading to changes in the pulse oximetry readings. However, inadequate contact with the tissue may result in movement of the sensor relative to the tissue, which may also be associated with measurement inaccuracies.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
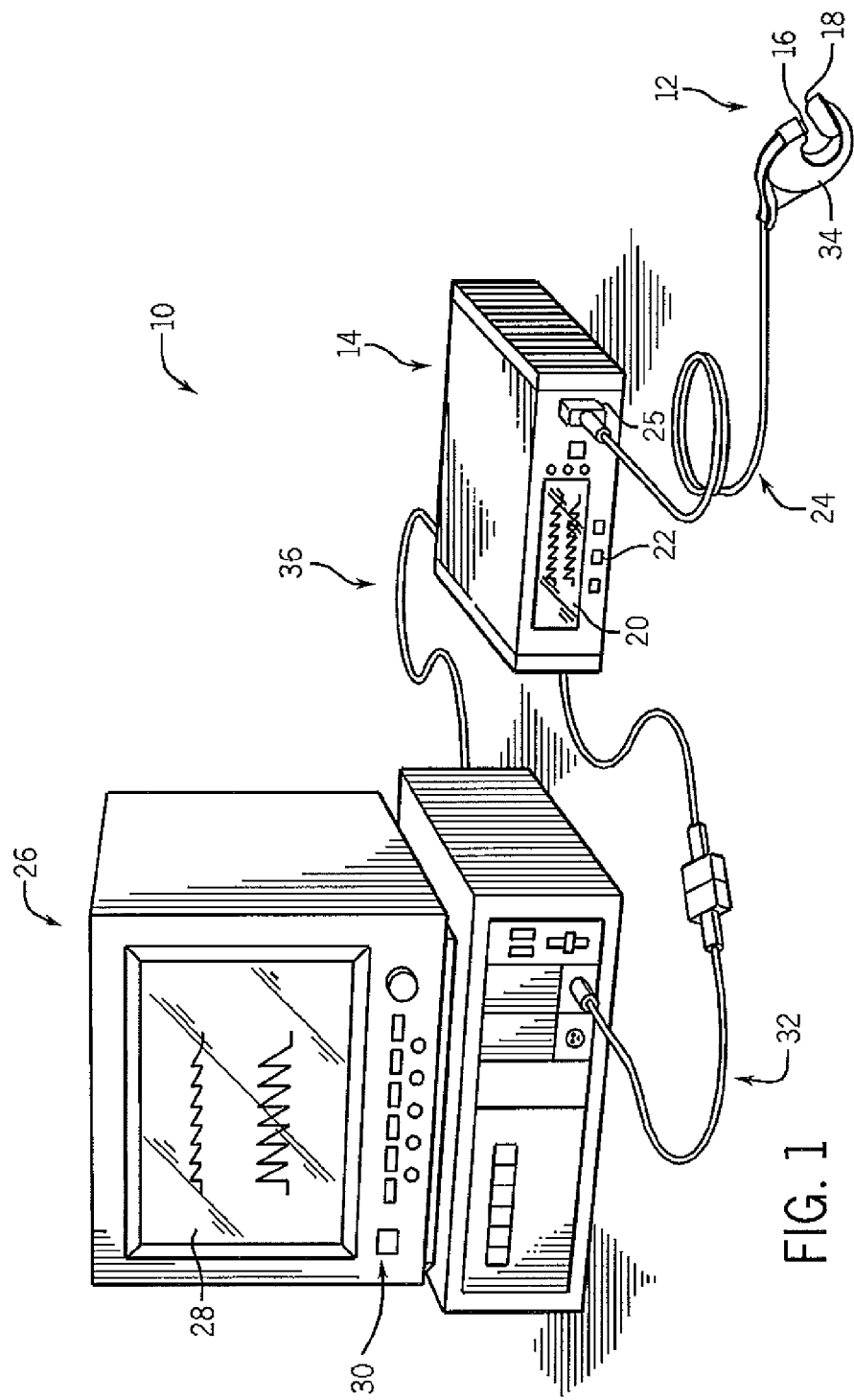
FIG. 1 is a front view of an embodiment of a monitoring system configured to be used with a photoplethysmography sensor as provided.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is generally directed to sensors for pulse oximetry or other applications utilizing spectrophotometry that, when applied to the tissue, apply a pressure sufficient to obtain sensor readings but not so great as to cause patient discomfort or result in signal artifacts. Further, the disclosed technique may be appropriate for other sensing modalities, including optical, electrical, chemical, acoustical, and/or ultrasound sensors. Optical sensors that are affixed to a patient's tissue are commonly applied via an adhesive, and/or a non-adhesive, non-slip bandage, and/or compressive force. For many clip-style sensors, e.g., finger sensors, a spring-loaded hinge biases opposing sides of the clip and provides the sensor application pressure to the appropriate tissue site. However, a finger or digit sensor may not be appropriate for a patient who has low blood perfusion in the limbs, for example in the case of low body temperature, shock, or sepsis. For such patients, alternate tissue sites such as the forehead, lip, nose, or ear may be better-perfused and, thus, may be associated with higher quality measurements. However, these sites may feature tissue to which it is difficult to apply a sensor because of the position or anatomy of each particular site. For example, a traditional clip-style sensor with a hinge may apply too much pressure to the tissue and may be uncomfortable for the patient. Further, such sensors may be bulky and heavy. Provided herein are sensors that are capable of applying pressure to opposing sides of a patient's tissue and that are lighter and more comfortable for the patient. Several embodiments remove the need for an elastic band or other external securing device, which reduces the workflow of the clinician applying the sensor and may provide a more stable pressure application over the use of the sensor. In particular embodiments, such sensors may employ an adjustable bladder that provides a customized fit for a particular patient. After the sensor is in place, the bladder may be inflated to adjust the fit to the desired pressure on the tissue. In this manner, patients of various sizes may use a one-size-fits-all sensor size. Further, because the pressure may be adjusted and/or monitored, the sensors as provided reduce the possibility of over- or under-pressurization at the tissue-contact site. Furthermore, in the event that a parameter depends on the tissue-pressure, it is possible that by dynamically adjusting the pressure during the monitoring cycle, further information about a parameter of interest may be extracted.

In other embodiments, the sensors provided herein may feature pressure application devices that are incorporated into the sensor. Such devices may be used in conjunction with sensors that apply force to opposing sides of a tissue (e.g., ear, lip, or digit sensors) or with sensors that are affixed to only one side of the tissue (e.g., a forehead sensor). In particular embodiments, the pressure application devices may include inflatable, deformable, or expandable structures, e.g., inflatable bladders or expanding foams, and/or bendable structures, such as metal strips. Such elements may facilitate coupling of the optical elements of the sensor with the tissue. In turn, the improved tissue-sensor contact may result in a reduction of sensor artifacts. In certain embodiments, such devices may be adjusted on a case-by-case basis and may be adjusted in response to low signal quality or feedback from a monitoring device. In addition, such sensors may also be used in conjunction with an external securing device (e.g., a headband). However, in certain embodiments, the disclosed sensors may be applied without an external securing device.

With this in mind, FIG. 1 depicts an embodiment of a patient monitoring system 10 that may be used in conjunction with a medical sensor 12. Although the depicted embodiments relate to sensors for use on a patient's forehead, digit, lip, or cheek, it should be understood that, in certain embodiments, the features of the multi-purpose sensor 12 as provided herein may be incorporated into sensors for use on other tissue locations, such as the forehead, finger, the toes, the heel, the ear, or any other appropriate measurement site. In addition, although the embodiment of the patient monitoring system 10 illustrated in FIG. 1 relates to photoplethysmography or pulse oximetry, the system 10 may be configured to obtain a variety of medical measurements with a suitable medical sensor. For example, the system 10 may, additionally be configured to determine tissue hydration, total hemoglobin, regional saturation, or any other suitable physiological parameter. As noted, the system 10 includes the sensor 12 that is communicatively coupled to a patient monitor 14. The sensor 12 includes one or more emitters 16 and one or more detectors 18. The emitters 16 and detectors 18 of the sensor 12 are coupled to the monitor 14 via a cable 24 through a plug 25 coupled to a sensor port. Additionally, the monitor 14 includes a monitor display 20 configured to display information regarding the physiological parameters, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing the techniques discussed herein.

The monitor 14 may be any suitable monitor, such as a pulse oximetry monitor available from Nellcor Puritan Bennett LLC. Furthermore, to upgrade conventional operation provided by the monitor 14 to provide additional functions, the monitor 14 may be coupled to a multi-parameter patient monitor 26 via a cable 32 connected to a sensor input port or via a cable 36 connected to a digital communication port, or via an RF or optical wireless link. In addition to the monitor 14, or alternatively, the multi-parameter patient monitor 26 may be configured to calculate physiological parameters and to provide a central display 28 for the visualization of information from the monitor 14 and from other medical monitoring devices or systems. The multi-parameter monitor 26 includes a processor that may be configured to execute code. The multi-parameter monitor 26 may also include various input components 30, such as knobs, switches, keys and keypads, buttons, etc., to provide for operation and configuration of the a multi-parameter monitor 26. In addition, the monitor 14 and/or the multi-parameter monitor 26 may be connected to a network to enable the sharing of information with servers or other workstations. In one embodiment, the sensor 12 may include a sensor body 34 housing the optical components (e.g., an emitter for emitting light at certain wavelengths into a tissue of a patient and a detector for detecting the light after it is reflected and/or absorbed by the blood and/or tissue of the patient) of the sensor. The sensor body 34 may be formed from any suitable material, including rigid or conformable materials, such as fabric, paper, rubber or elastomeric compositions (including acrylic elastomers, polyimide, silicones, silicone rubber, celluloid, PMDS elastomer, polyurethane, polypropylene, acrylics, nitrile, PVC films, acetates, and latex).

In certain embodiments, the sensor 12 may be a wireless sensor 12. Accordingly, the wireless sensor 12 may establish a wireless communication with the patient monitor 14 and/or the multi-parameter patient monitor 26 using any suitable wireless standard. By way of example, the wireless module may be capable of communicating using one or more of the ZigBee standard, WirelessHART standard, Bluetooth standard, IEEE 802.11x standards, or MiWi standard. In embodiments in which the sensor 12 is configured for wireless communication, the strain relief features of the cable 24 may be housed in the sensor body 34.

As provided herein, the sensor 12 may be a sensor suitable for detection of one or more physiological parameters. The sensor 12 may include optical components (e.g., one or more emitters 16 and detectors 18). In one embodiment, the sensor 12 may be configured for photo-electric detection of blood and tissue constituents. For example, the sensor 12 may include pulse oximetry sensing functionality for determining the oxygen saturation of blood as well as other parameters from the plethysmographic waveform detected by the oximetry technique. An oximetry system may include a light sensor (e.g., sensor 12) that is placed at a site on a patient, typically a fingertip, toe, forehead or earlobe, or in the case of a neonate, across a foot. The sensor 12 may pass light using the emitter 16 through blood perfused tissue and photoelectrically sense the absorption of light in the tissue. For example, the monitor 14 may measure the intensity of light that is received at the light sensor as a function of time. A signal representing light intensity versus time or a mathematical manipulation of this signal (e.g., a scaled version thereof, a log taken thereof, a scaled version of a log taken thereof; etc.) may be referred to as the photoplethysmograph (PPG) signal. The light intensity or the amount of light absorbed may then be used to calculate the amount of the blood constituent (e.g., oxyhemoglobin) being measured and other physiological parameters such as the pulse rate and when each individual pulse occurs. Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. At least two, e.g., red and infrared (IR), wavelengths may be used because it has been observed that highly oxygenated blood will absorb relatively less red light and more infrared light than blood with a lower oxygen saturation. However, it should be understood that any appropriate wavelengths, e.g., green, etc., may be used as appropriate. Further, photoplethysmography measurements may be determined based on only one, two, or three or more wavelengths of light.

Figure 2:
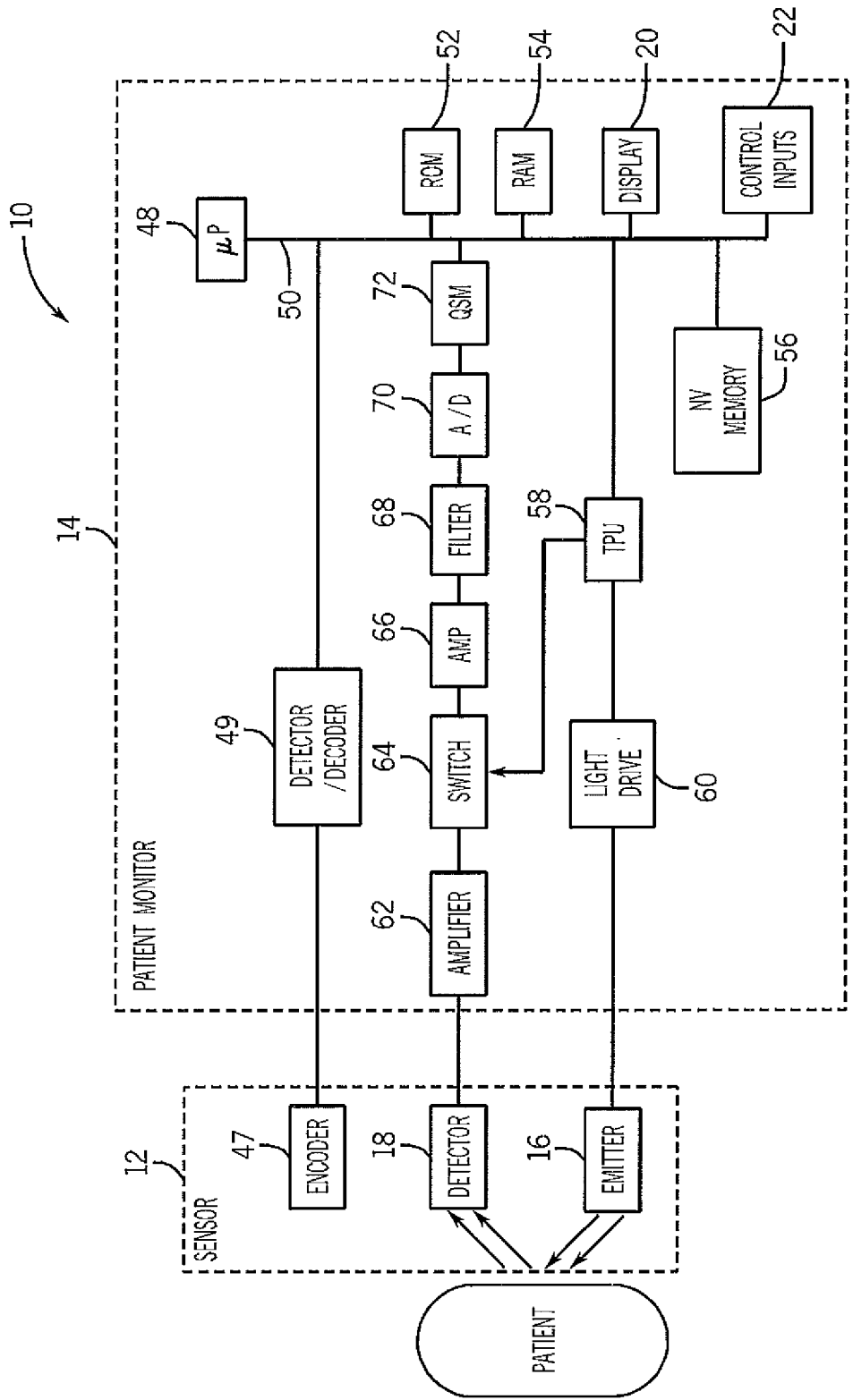
FIG. 2 is a block diagram of the monitoring system of FIG. 1.

Turning to FIG. 2, a simplified block diagram of the medical system 10 is illustrated in accordance with an embodiment. As noted, the sensor 12 may include optical components in the forms of emitters 16 and detectors 18. The emitter 16 and the detector 18 may be arranged in a reflectance or transmission-type configuration with respect to one another. However, in embodiments in which the sensor 12 is configured for use on a patient's forehead (e.g. either alone or in conjunction with a hat or headband), the emitters 16 and detectors 18 may be in a reflectance configuration. Such sensors 12 may be used for pulse oximetry or regional saturation monitoring (e.g., INVOS® monitoring). An emitter 16 may also be a light emitting diode, superluminescent light emitting diode, a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements, absorptive filters, dielectric stack filters, or interferometers. These kinds of emitters and/or detectors would typically be coupled to the sensor 12 via fiber optics. Alternatively, a sensor assembly 12 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects in conjunction with the appropriate sensing elements.

In certain embodiments, the emitter 16 and detector 18 may be configured for pulse oximetry. It should be noted that the emitter 16 may be capable of emitting at least two wavelengths of light, e.g., red and infrared (IR) light, into the tissue of a patient, where the red wavelength may be between about 600 nanometers (nm) and about 700 nm, and the IR wavelength may be between about 800 nm and about 1000 nm. The emitter 16 may include a single emitting device, for example, with two LEDs, or the emitter 16 may include a plurality of emitting devices with, for example, multiple LED's at various locations. In some embodiments, the LEDs of the emitter 16 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940 nm (e.g., 900 nm). Other wavelengths may include, for example, wavelengths of between approximately 500-600 nm and/or 1000-1100 nm and/or 1200-1400 nm. Regardless of the number of emitting devices, light from the emitter 16 may be used to measure, for example, oxygen saturation, water fractions, hematocrit, or other physiologic parameters of the patient. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In another embodiment, two emitters 16 may be configured for use in a regional saturation technique. To that end, the emitters 16 may include two light emitting diodes (LEDs) that are capable of emitting at least two wavelengths of light, e.g., red or near infrared light. In one embodiment, the LEDs emit light in the range of 600 nanometers to approximately 1000 nm. In a particular embodiment, one LED is capable of emitting light at 730 nm and the other LED is capable of emitting light at 810 nm.

In any suitable configuration of the sensor 12, the detector 18 may be an array of detector elements that may be capable of detecting light at various intensities and wavelengths. In one embodiment, light enters the detector 18 after passing through the tissue of the patient. In another embodiment, light emitted from the emitter 16 may be reflected by elements in the patent's tissue to enter the detector 18. The detector 18 may convert the received light at a given intensity, which may be directly related to the absorbance and/or reflectance of light in the tissue of the patient, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. The detector 18 may receive light that has not entered the tissue to be used as a reference signal. After converting the received light to an electrical signal, the detector 18 may send the signal to the monitor 14, where physiological characteristics may be calculated based at least in part on the absorption and/or reflection of light by the tissue of the patient.

In certain embodiments, the medical sensor 12 may also include an encoder 47 that may provide signals indicative of the wavelength of one or more light sources of the emitter 16, which may allow for selection of appropriate calibration coefficients for calculating a physical parameter such as blood oxygen saturation. The encoder 47 may, for instance, be a coded resistor, EEPROM or other coding devices (such as a capacitor, inductor, PROM, RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 47 may include encryption coding that prevents a disposable part of the medical sensor 12 from being recognized by a microprocessor 48 unable to decode the encryption. For example, a detector/decoder 49 may translate information from the encoder 47 before it can be properly handled by the processor 48. In some embodiments, the encoder 47 and/or the detector/decoder 48 may not be present. In some embodiments, the encrypted information held by the encoder 47 may itself be transmitted via an encrypted data protocol to the detector/decoder 49, such that the communication between 47 and 49 is secured.

Signals from the detector 18 and/or the encoder 47 may be transmitted to the monitor 14. The monitor 14 may include one or more processors 48 coupled to an internal bus 50. Also connected to the bus may be a ROM memory 52, a RAM memory 54, non-volatile memory 56, a display 20, and control inputs 22. A time processing unit (TPU) 58 may provide timing control signals to light drive circuitry 60, which controls when the emitter 16 is activated, and if multiple light sources are used, the multiplexed timing for the different light sources. TPU 58 may also control the gating-in of signals from detector 18 through a switching circuit 64. These signals are sampled at the proper time, depending at least in part upon which of multiple light sources is activated, if multiple light sources are used. The received signal from the detector 18 may be passed through one or more amplifiers (e.g., amplifiers 62 and 66), a low pass filter 68, and an analog-to-digital converter 70 for amplifying, filtering, and digitizing the electrical signals from the sensor 12. The digital data may then be stored in a queued serial module (QSM) 72, for later downloading to RAM 54 as QSM 72 fills up. In an embodiment, there may be multiple parallel paths for separate amplifiers, filters, and AID converters for multiple light wavelengths or spectra received.

In an embodiment, based at least in part upon the received signals corresponding to the light received by detector 18, processor 48 may calculate the oxygen saturation using various algorithms. These algorithms may use coefficients, which may be empirically determined. For example, algorithms relating to the distance between an emitter 16 and various detector elements in a detector 18 may be stored in a ROM 52 and accessed and operated according to processor 48 instructions. Furthermore, one or more functions of the monitor 14 may also be implemented directly in the sensor 12. For example, in some embodiments, the sensor 12 may include one or more processing components capable of calculating the physiological characteristics from the signals obtained from the patient. In accordance with the present techniques, the sensor 12 may be configured to provide optimal contact between a patient and the detector 18, and/or the emitter 16. The sensor 12 may have varying levels of processing power, and may output data in various stages to the monitor 14, either wirelessly or via the cable 24 (see FIG. 1). For example, in some embodiments, the data output to the monitor 14 may be analog signals, such as detected light signals (e.g., pulse oximetry signals), or processed data.

Figure 3:
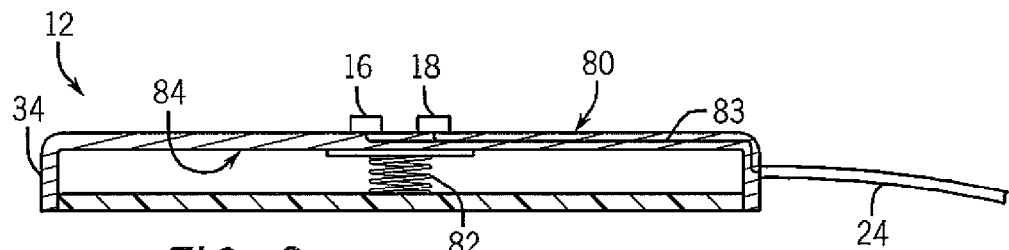
FIG. 3 is a section view of sensor including an example of a deformable element in the form of a spring and that is configured to be used in conjunction with the monitoring system of FIG. 1.
Figure 4:
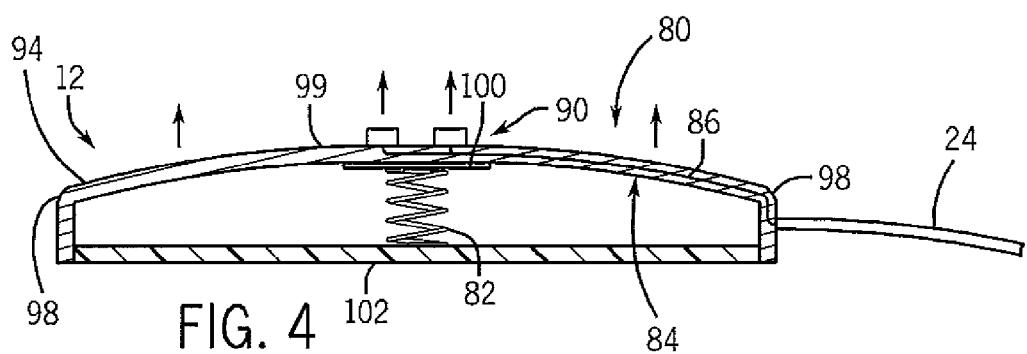
FIG. 4 is a section view of the sensor of FIG. 3 in an expanded or deformed configuration.

The sensors 12 as provided herein may be capable of expanding against or applying pressure to the patient's tissue to hold the optical elements of the sensor 12 in place while physiological monitoring is conducted. Detection of small signals may involve pressure stability and/or dialing in pressure for highest signal. For that reason the sensors 12 may be used in conjunction with pre-determined or settable pressure. In one embodiment, the sensor 12 is a conformable sensor with optical elements (e.g., one or more emitters 16 and detectors 18) disposed on the sensor body 34 on a tissue-contact surface 80 in any suitable configuration with respect to one another. For example, as shown in FIG. 3, the emitter 16 and detector 18 may be in a reflectance configuration. However, the disclosed embodiments may also be incorporated into transmission-type sensors. The sensor 12 includes a deformable element, illustrated here as a spring 82 that expands to push the sensor body 34 into a generally non-planar configuration in the absence of any biasing forces (e.g., when the sensor is placed on a flat surface), as shown in FIG. 4. It should be understood that an adhesive may be used in conjunction with any of the disclosed embodiments for at least partially securing the sensor 12 to the patient. For example, the surface 80 may include an adhere-to-skin-adhesive that is strong enough to oppose the relaxed shape of the sensor, but light enough to remove from the skin without discomfort. Further, the adhesive may be applied to all or only part of the surface 80, e.g., the periphery of the surface 80. The emitter 16 and detector 18 are coupled to the cable 24 by leads 83 that are configured to allow movement of the sensor 12 from a planar to a non-planar configuration as the spring 82 expands. For example, the leads 83 may be configured to flex, move, or unfold as the sensor 12 changes configuration. While certain embodiments include the spring 82, it should be understood that any suitable deformable element may be incorporated into the disclosed configurations.

The spring 82 is positioned to be in contact with an opposing surface 84, i.e., behind a substrate 86 on which the emitter 16 and detector 18 are disposed to facilitate pushing the optical elements against the tissue. In this manner, the pressure applied to the tissue may vary across the tissue contact surface 80. For example, in the area 90 of the tissue contact surface 80 corresponding to the emitter 16 and the detector 18, the pressure may be higher than in the areas 94 and 96 towards the corners 98 of the sensor body 34. Further, the spring 82 may be coupled to a plate 100 that is adapted to spread the spring force across its surface so that the pressure applied by the emitter 16 and the detector 18 to the tissue is about equal. The size and surface area of the plate 100 may be selected to achieve a desired distribution of pressure across the tissue-contact surface 80. For example, a large plate 100 may result in a larger area of lower pressure relative to the corners 94 and 98. Such an embodiment may be beneficial for spreading the spring force to minimize pressure contact marks from the optical components. On the other hand, a smaller plate 100 may direct the pressure to the area 90 corresponding to the optical components, which may improve sensor-tissue contact. It should be understood that, while the emitter 16 and the detector 18 are illustrated as protruding from the tissue-contact surface 80, the disclosed embodiments may also be used in conjunction with optical components that are embedded in, flush with, or recessed in the sensor body 34.

Figure 5:
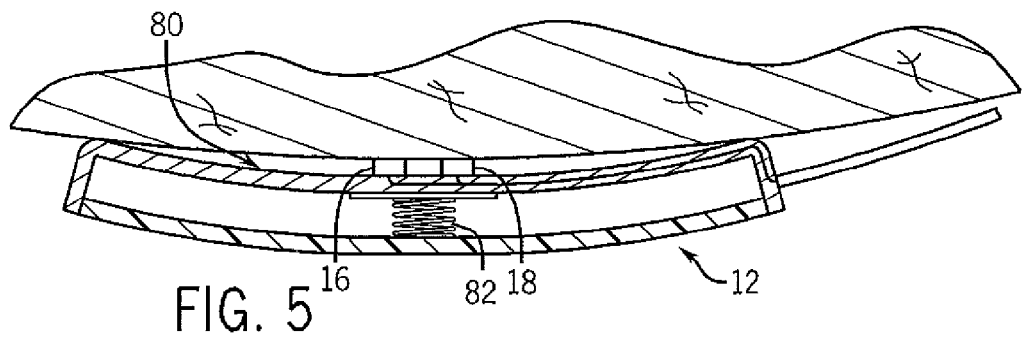
FIG. 5 is a view of the sensor of FIG. 3 applied to a patient.

To accommodate the deforming action of the deformable element, the sensor body 34 may be assembled to allow a portion of the sensor 12 to form a protrusion 99, e.g., a dome or barb-shaped formation along the tissue-contact surface 80. In one embodiment, the spring 82 is positioned on a backing layer 102. The backing layer 102 and the substrate 86 on which the emitter 16 and the detector 18 are disposed are not adhered to one another in at least the area 90 to allow expansion of the spring 82 (or other deformable element). Further, the deformable element may be configured to apply a desired amount of pressure to the tissue. In an embodiment in which the deformable element is a spring 82, the materials and winding of the spring 82 may be selected to achieve an appropriate amount of spring force. In any of the disclosed embodiments, the pressure applied to the tissue may be greater than a venous pressure but less than an arterial pressure. Such pressures may vary depending on a patient's physiological condition, but in one embodiment, the pressure applied by the sensor 12 is at least 3-5 mm Hg or at least 10 mm Hg. When the sensor 12 is applied to a patient's forehead, as shown in FIG. 5, the spring 82 may push against the tissue to hold the emitter 16 and detector 18 against the forehead. The sensors 12 may also feature additional coupling devices, including adhesives disposed on the tissue-contact layer 80.

The total pressure applied by the sensor 12 may be a function of the pressure applied by all of the coupling devices of the sensor 12. For example, an adhesively-applied sensor 12 may apply a pressure that is supplemented by the spring force of the spring 82 to achieve a total desired pressure. If used in conjunction with a device such as a headband, the sensor 12 may be applied with positive pressure, and the plate 100/spring 82 combination may apply additional pressure over the sensing site. If the sensor is applied with adhesive but with no headband or other securing device, the portion of the surface 80 with the adhesive may pull on the skin to create some negative pressure areas. Accordingly, the pressure over the tissue-contact surface 80 may vary depending on the adhesive used, the location of the adhesive on the surface 80, the size and shape of the plate 100, and the presence or absence of additional securing devices. In addition, the sensor 12 is configured such that, when applied to the tissue, the deformable element is not fully extended or deformed. In this manner, the spring 82 applies consistent pressure to the tissue. Depending on the conformability or rigidity of the backing layer 102 as well as the total spring force of the deformable element, the spring 82 may also provide spring force to push the sensor 12 away from the tissue. The adhesive layer may serve to oppose any such effects, resulting in the appropriate amount of applied force over the plate 100, where the sensing occurs. A slightly more rigid backing layer (e.g., conformable, but relatively more rigid than the substrate 86) may also serve to direct the force of the spring 82 towards the tissue.

Figure 6:
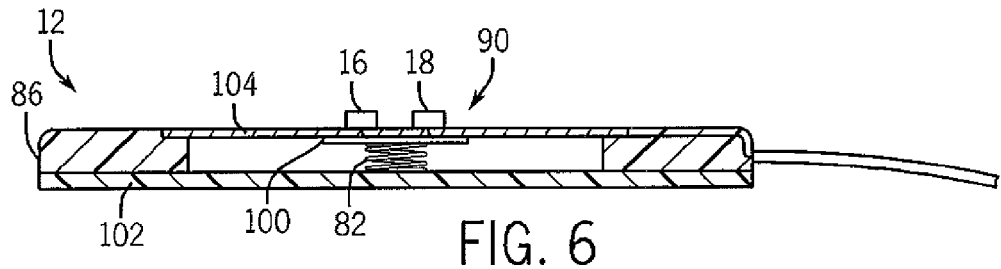
FIG. 6 is a view of an alternative sensor in which the sensor body includes an elastic portion to accommodate expansion of the spring.
Figure 7:
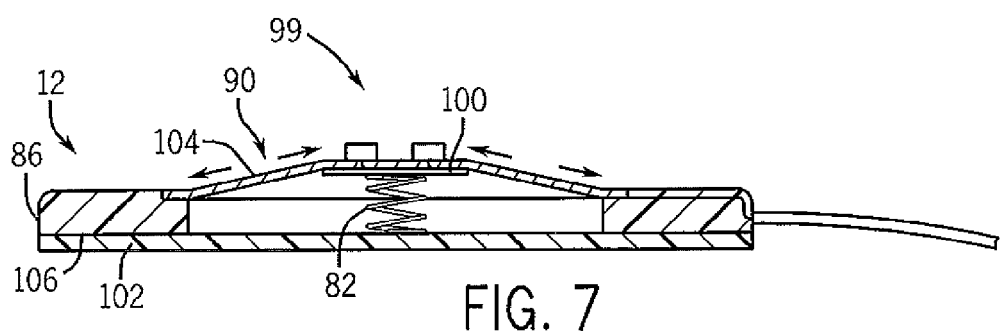
FIG. 7 is a view of the sensor of FIG. 6 in an expanded configuration.
Figure 8:
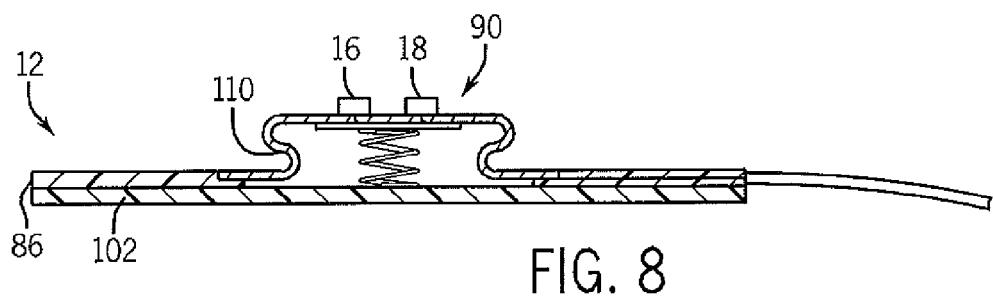
FIG. 8 is a view of an alternative sensor in which the sensor body includes pleats or folds to accommodate expansion of the spring.

The assembly of the sensor 12 may facilitate expansion of the deformable element. For example, at least the area 90 of the tissue-contact surface 80 that corresponds to the emitter 16 and the detector 18 may be formed from an elastic material 104 to accommodate expansion of the spring 82, as shown in FIG. 6. In such embodiments, the rest of the substrate 80 may either be formed from elastic or inelastic materials. If the entire tissue-contact surface is elastic, adhesion to backing layer 102 may restrict expansion in undesired areas of the sensor. In other embodiments, the substrate 80 may be formed from a generally inelastic material that includes some slack to accommodate the expansion. In certain embodiments, the surface 80 may contain an adhesive to oppose relaxed shape of sensor and adhere to sensing site. For example, as shown in FIG. 8, the substrate 80 may include folds or pleats 110 such that, when the deformable element is in a restrained state, the substrate 80 is in a planar configuration. When the deformable element is released from the restrained state, the folds 104 may expand to the sensor 12 to apply pressure to the tissue.

Figure 9:
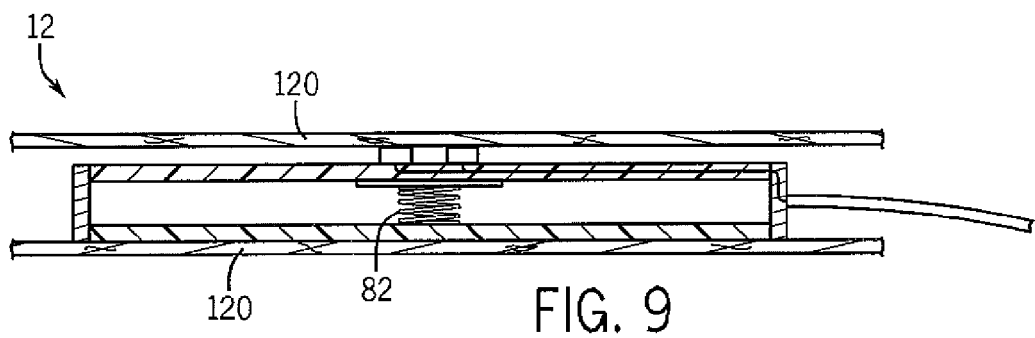
FIG. 9 is a view of a sensor including one or more release layers that hold the sensor in a generally planar configuration.

As noted, the sensor 12 may be able to move from a restrained, planar configuration to an unrestrained non-planar configuration when any biasing forces are removed. For example, when the sensor 12 is applied to the patient, the tissue applies a biasing force to the sensor 12 that may push any protrusion 99 (see FIG. 4) towards the backing layer 102 such that the sensor 12 is either generally planar or between the planar and fully deformed configurations. In addition, the sensor 12 may be stored or packaged in a planar configuration, such as with one or more rigid release layers 120 that are formed from material capable of holding the sensor 12 in a generally planar configuration, as shown in FIG. 9. In other embodiment, the spring 82 may be restrained by a string or clip that may be removed by an operator prior to use.

Figure 10:
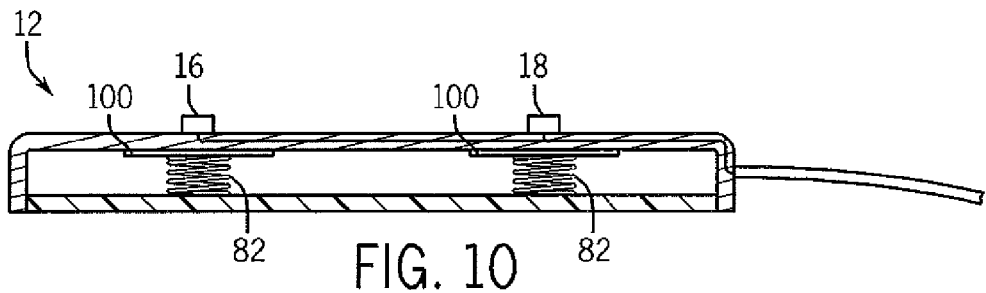
FIG. 10 is a view of a sensor including multiple spring elements.

In certain embodiments, the sensor 12 may include a plurality of deformable elements. For example, as shown in FIG. 10, the emitter 16 and the detector 18 may each be coupled to respective springs 82 and plates 100. In one embodiment, the depicted sensor 12 may be used for transmission-type arrangements. Alternatively, depending on the desired tissue application site, the sensor 12 may be use a mix of deformable elements. For example, the sensor 12 may include a spring 82 and an inflatable bladder or bendable element.

Figure 11:
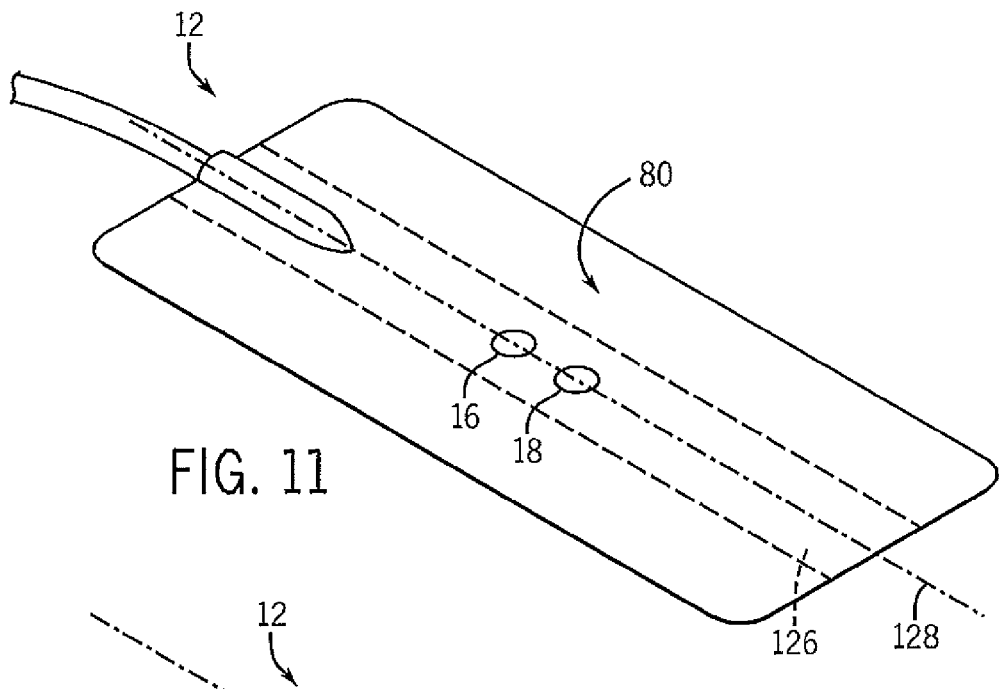
FIG. 11 is a view of a sensor in which the deformable element is a bendable strip.
Figure 12:
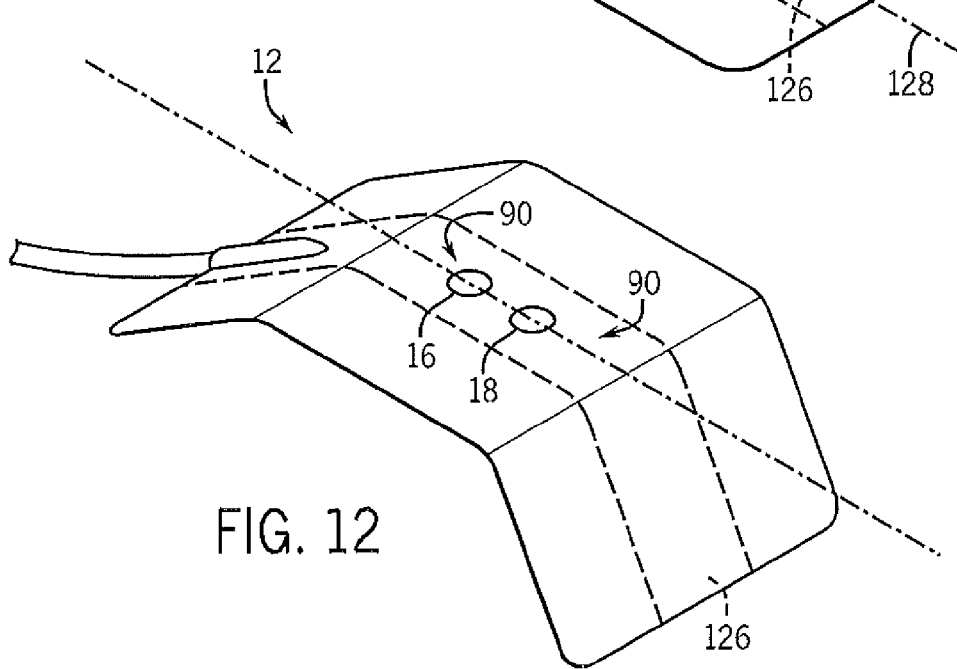
FIG. 12 is a view of the sensor of FIG. 11 in a bent configuration.

In addition to springs, suitable deformable elements may include bendable components. FIG. 11 shows an embodiment in which the sensor 12 includes a deformable layer 126 that may be shaped by the operator to push the emitter 16 and the detector 18 towards the tissue, as shown in FIG. 12. In this manner, the sensor 12 may be fit on a patient-by-patient basis. The deformable layer 126 may be formed from metal or suitable polymers that are capable of being bent by hand. For example, the deformable layer 126 may be formed from aluminum, copper, brass, or combinations of such. In other embodiments, the deformable layer 126 may be a series of wires or wire mesh. Such embodiments may provide lighter weight sensors. In particular, the deformable layer may be formed from materials that retain their shape when bent so that any formed protrusions 99 or formed curves remain generally stable when the sensor 12 is applied to the patient. The deformable layer 126 may, in particular embodiments, be formed from a shape memory material. In such embodiment, the deformable layer 126 may act like a spring and may assume a configuration that applies pressure to the patient's tissue under particular conditions (e.g., release of a biasing force, a change in temperature, an applied current, etc). Depending on the composition of the deformable layer 126, the sensor 12 may also include appropriate shielding layers to reduce cross-talk and interference.

The deformable layer 126 may be the same size as the tissue-contact surface 80, which may provide greater flexibility in shaping the entire sensor 12 against the tissue. In other embodiments, the deformable layer 126 may be positioned to correspond to only a portion of the total area of the tissue contact surface 80, e.g., corresponding to the area 90 or less than about 50% or less than about 20% of the tissue-contact surface 80. Further, the deformable layer 120 may be positioned along an imaginary axis 128 connecting the emitter 16 and the detector 18 to facilitate proper placement of the optical components against the tissue.

Figure 13:
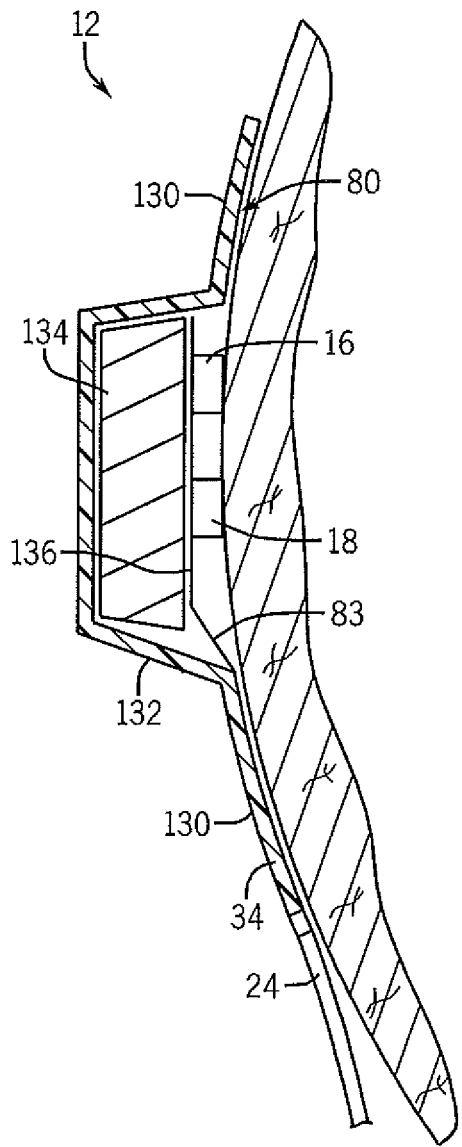
FIG. 13 is a view of a sensor in which the deformable element is a compressible foam.

FIG. 13 illustrates an embodiment in which the sensor 12 includes a compressible foam that pushes the optical components against the tissue. In the depicted embodiment, the sensor body 34 forms a cup 132 surrounded by wings 130 that affix the sensor 12 to the tissue, e.g., via an adhesive layer. The cup 132 may be formed from a semi-rigid material (e.g., a thin plastic) that maintains the shape of the sensor body 34. The wings 130 may be formed from the same material for ease of manufacturing or may more conformable for patient comfort. A foam pad 134 is positioned within the cup 132 and is sized such that, when expanded in an unrestrained manner (e.g., when not applied to a patient), the foam pad 134 expands outside of the cup 132. When applied to a patient, the foam pad 134 is only permitted to expand to the point of tissue contact. In this manner, the foam pad 134 applies pressure through its expansion. The emitter 16 and detector 18 may rest on a substrate 136 that translates the force of the foam pad 134. The wire leads 83 may run along or within the wings 130 and couple to the cable 24. The material from which the cup 132 is formed may be selected to resist buckling from the force of expansion of the foam pad 134 such that the force of the expansion is translated towards the tissue. In particular embodiments, the foam pad 134 may be an activated material that expands upon contact with a liquid or gel.

Figure 14:
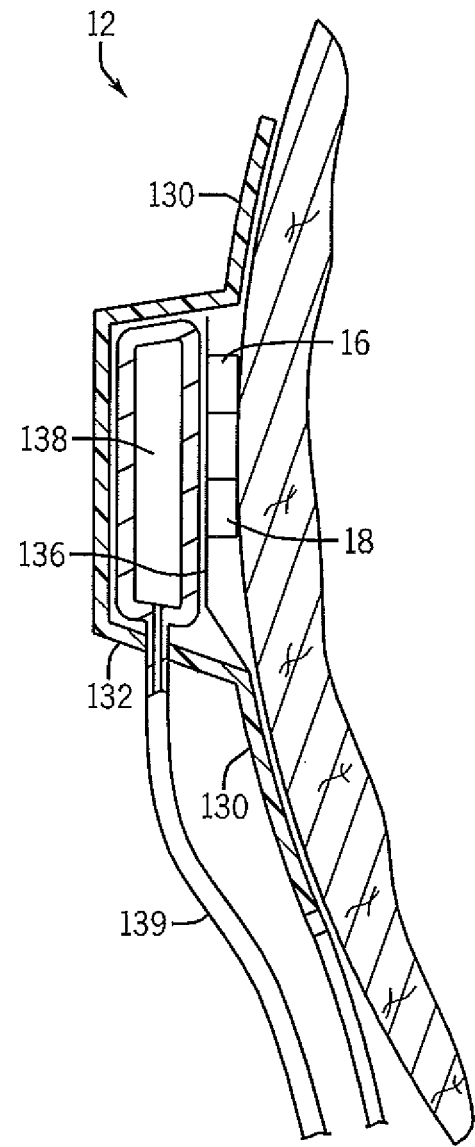
FIG. 14 is a view of a sensor in which the deformable element is an air bladder.

FIG. 14 is alternate embodiment in which the sensor 12 includes an inflatable bladder 138 positioned within the cup 132. Inflation of the bladder 138 pushes the substrate 136 holding the emitter 16 and the detector 18 against the tissue. An inflation line 139 is accessible to an operator to connect to an external fluid source. Inflation of the bladder 138 may be accomplished via a syringe coupled to an inflation port or via a pumping mechanism that is controlled by the monitor 14. In particular embodiments, the bladder 138 is inflated or deflated in response to signal quality feedback from the monitor 14. In low signal quality cases, the inflation of the bladder 138 may be adjusted until the signal quality improves under the control of the monitor 14. The inflation bladder 138 may be sized and shaped such that, when inflated the bladder 138 engages with the substrate 130 without significant material stretch within the walls of the bladder 138.

Figure 15:
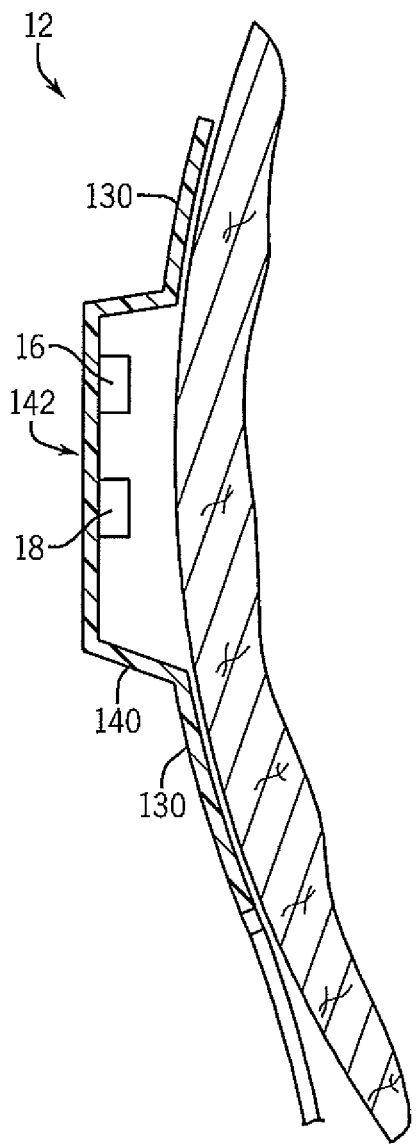
FIG. 15 is a view of a sensor in which the deformable element is an invertable button.
Figure 16:
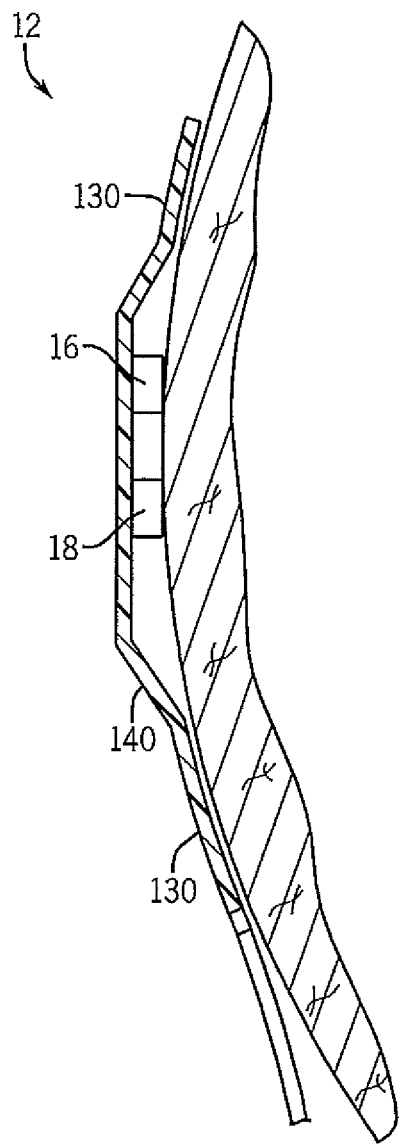
FIG. 16 is a view of the sensor of FIG. 15 with the button in the inverted state.

FIG. 15 illustrates an embodiment in which the sensor 12 includes a deformable button 140 that may be popped out or inverted along arrow 142 as shown in FIG. 16 to position the emitter 16 and the detector 18 against the tissue. In certain embodiments, the button 140 may be formed form a thermoplastic material. Depending on the application, inverting the button may strain the material past its elastic deformation point such that, once inverted, the button 140 cannot assume its pre-inverted conformation. In this manner, the sensor 12 may be clearly indicated as already used to prevent improper re-use. In other embodiments, the button 140 may be bi-stable or multi-stable, such that the sensor 12 may be re-armed and re-used, if sensor repositionability is desirable. The button 140 may be similar to a button on a coffee lid and, in one embodiment, may be formed from the same material as the wings 130 but may be extruded or molded as a thinner diaphragm.

Figure 17:
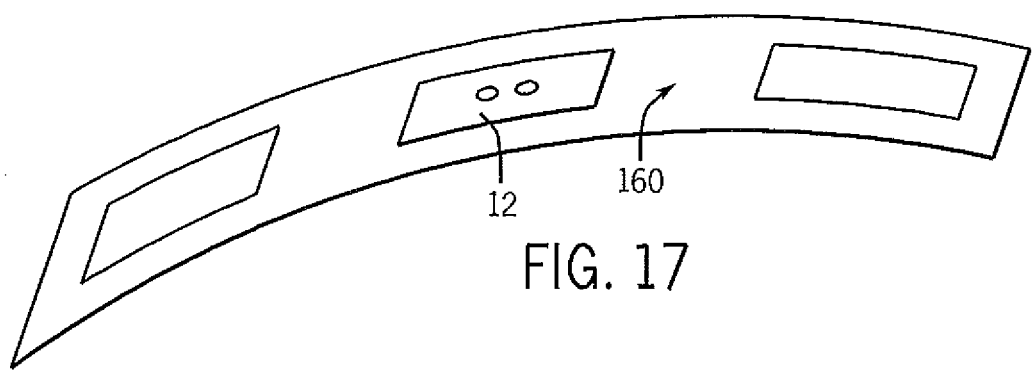
FIG. 17 is a view of a headband including a sensor with a deformable element.
Figure 18:
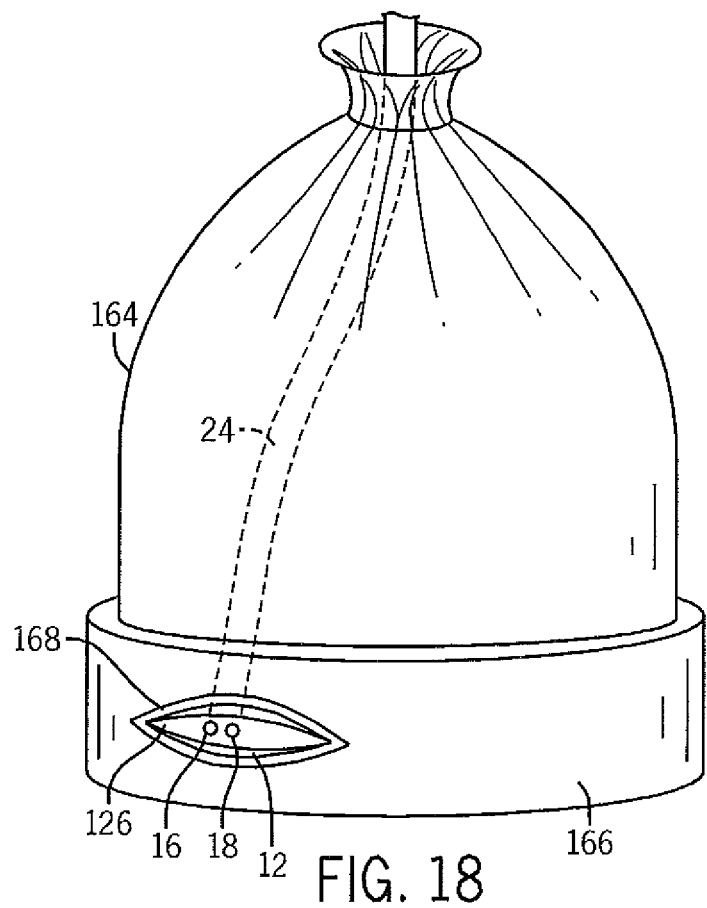
FIG. 18 is a view of a hat including a sensor with a deformable element.

The sensors 12 as provided may be incorporated into structures for coupling the optical elements to the tissue, such as a hat, a headband, or semi-rigid or rigid headgear. In one embodiment, the sensor 12 may be incorporated onto an interior face 160 of a headband to affix the sensor 12 to a forehead, as shown in FIG.17. In another embodiment, the sensors may be incorporated into a hat 164, as shown in FIG. 18. The sensor 12 may be positioned on the brim 166 of the hat to facilitate positioning of the sensor 12 on the forehead. In addition, the hat 164 may include a window 168 positioned to allow operator manipulation of the sensor 12. In the depicted embodiment, the sensor 12 includes a deformable layer 126 that the operator may bend to position the optical elements against the tissue. As noted, such structures may provide additional pressure to the tissue.

Figure 19:
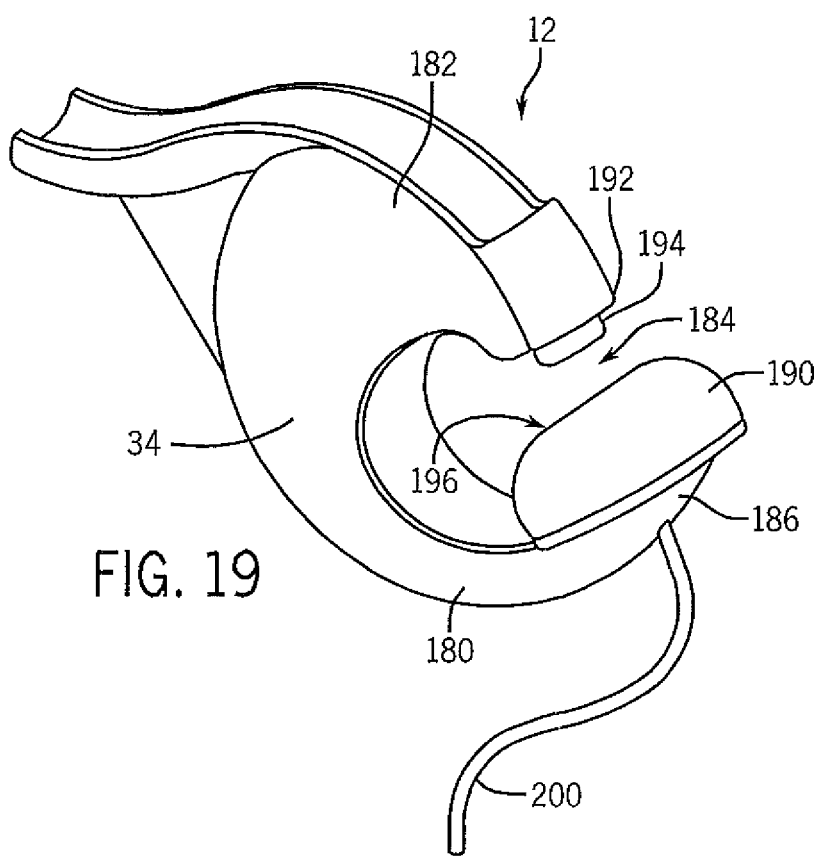
FIG. 19 is a view of a rigid sensor in which the deformable element is an air bladder.

In an alternative embodiment, the deformable elements may be coupled to rigid (e.g., reusable) sensors 12 for affixing optical elements to the tissue. FIG. 19 illustrates an embodiment of a sensor 12 that may be appropriate for placement on an ear, lip, nostril, or cheek of a patient. Affixing traditional clip-style sensors to such sites is complex because the tissue is not supported by bones. Accordingly, the sensors may not apply undue pressure to the site without patient discomfort. Further, the position of these tissue sites may result in the weight of a traditional clip-style sensor, once applied, hanging down, which may result in movement of the sensor relative to the patient. In addition, traditional adhesives may not be effective on the mucosal tissue of the cheek or lip. Provided herein are sensors 12 that incorporate a jaw or open clip structure but that don't include a hinge. Such sensors 12 are fitted to the patient with a deformable element that expands to fit the patient.

The sensor 12 includes a rigid sensor body 34 that includes a first member 180 and a second member 182 that are configured to be positioned on opposing sides of the patient's tissue when applied to the patient. That is, the tissue fits into opening 184 to complete the partial annulus of the sensor body 34. The end 186 of the first member 180 terminates in a deformable element, shown here as an inflatable bladder 190. The end 192 of the second member 182 terminates in a substrate 194 (e.g., a rigid substrate) that houses the optical components of the sensor 12 in a reflectance configuration. The sensor 12 may also be configured in transmission configuration. In such an embodiment, an optical element may be associated with a tissue-contact surface 196 of the inflatable bladder 190. For the transmission case, the receiving element can also be inside the inflatable bladder 190, whether in intimate contact with the inside of the bladder, or in contact with the surface of 186 that lies within the bladder, or alternatively suspended within the bladder 190. The inflatable bladder 190 is coupled to an inflation line 200 that may be run through the sensor body 34.

The sensor body 34 may be formed as a unitary assembly. For example, the sensor body 34 may be a molded structure. Further, the first member 180 and the second member 182 may be part of a single continuous piece and may be in a fixed position relative to one another. In contrast to a clip-type sensor, the first member 180 and the second member 182 do not move towards one another. Instead, the sensor 12 is loosely fitted to the patient and the inflatable bladder 190 is expanded to fill any intervening space until the appropriate pressure has been applied and the sensor 12 is in place. In other embodiments, the sensor body 34 may include a spring that applies part of the pressure to the tissue (e.g., less than 20 mm Hg) and the inflatable bladder 190 provides the rest of the pressure.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. For example, elements of the disclosed components may be exchanged or combined as appropriate. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A sensor, comprising:
 a conformable sensor body having a tissue-contact surface;
 an emitter and detector disposed on the tissue-contact surface in a reflectance configuration; and
 a deformable element disposed on the sensor body on a surface opposing the emitter and the detector, wherein the deformable element comprises a material having a deformation point, and wherein the deformable element is configured to cause a portion of the sensor body to protrude against a patient's tissue when the sensor is applied to the patient's tissue and when a force is applied to the deformable element that exceeds the deformation point of the material such that the pressure applied by the sensor body is non-uniform across the tissue-contact surface and is highest in the area of the sensor body proximate to the emitter and the detector.

2. The sensor of claim 1, wherein the sensor is configured to be applied to a patient's forehead.

3. The sensor of claim 1, wherein the sensor is disposed on an interior portion of a hat.

4. The sensor of claim 1, wherein the sensor is disposed on an interior portion of a headband, or semi-rigid or rigid headgear.

5. The sensor of claim 1, wherein the sensor is disposed in a window of a hat or a headband such that the sensor is visible to an observer when the hat is applied to a patient.

6. The sensor of claim 1, wherein the deformable element is adapted to cause the sensor body to apply sufficient pressure to the patient's tissue to overcome venous pressure but not arterial pressure.

7. The sensor of claim 1, wherein the deformable element covers less than 20% of the opposing surface sensor body.

8. The sensor of claim 1, wherein the deformable element comprises a foam, wherein when the foam is compressed with a biasing force, the tissue-contact surface has a generally planar configuration and wherein when the biasing force is removed, the tissue-contact surface has a generally non-planar configuration.

9. The sensor of claim 1, wherein the deformable element is not capable of resuming an un-deformed conformation after being deformed.

10. The sensor of claim 1, wherein the sensor comprises a photoplethysmography sensor.

11. A sensor, comprising:
a conformable sensor body having a tissue-contact surface;
an emitter or a detector disposed on the tissue-contact surface in a reflectance configuration; and
a deformable element disposed on the sensor body on a surface opposing the emitter and the detector, wherein the deformable element is configured to cause the sensor body to assume a first non-planar configuration, wherein the first non-planar configuration is stable in the absence of a biasing force, and wherein the deformable element is configured to cause the sensor body to assume a second non-planar configuration when a force above a predetermined threshold is applied to the deformable element, and wherein the force above the predetermined threshold strains the deformable element past a deformation point of the deformable element such that the sensor body is not capable of resuming the first non-planar configuration after the sensor body assumes the second non-planar configuration.

12. The sensor of claim 11, wherein the deformable element comprises a thermoplastic dome or button.

13. A sensor, comprising:
a conformable sensor body having a tissue-contact surface;
an emitter and detector disposed on the tissue-contact surface in a reflectance configuration; and
a deformable element on the conformable sensor body on a surface opposing the emitter and the detector, wherein the deformable element is in a first configuration, and wherein the deformable element assumes a second configuration when a force above a predetermined threshold is applied to the deformable element, and wherein the deformable element is not capable of resuming the first configuration after the deformable element assumes the second configuration.

14. The sensor of claim 13, wherein the sensor comprises a photoplethysmography sensor.

15. The sensor of claim 13, wherein the deformable element comprises a thermoplastic dome or button.

* * * * *